US006051589A

United States Patent [19]

Kanellakopulos et al.

[11] Patent Number: 6,051,589

[45] Date of Patent: *Apr. 18, 2000

[54] DIPHENYLOXAZOLINE DERIVATIVES

[75] Inventors: Johannes Kanellakopulos, Dormagen; Gerd Kleefeld, Neuss-Üdesheim; Udo Kraatz, Leverkusen; Ulrike Wachendorff-Neumann, Neuwied; Christoph Erdelen, Leichlingen; Andreas Turberg, Erkrath; Norbert Mencke, Leverkusen, all of Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/676,129

[22] PCT Filed: Jan. 4, 1995

[86] PCT No.: PCT/EP95/00022

§ 371 Date: Jul. 9, 1996

§ 102(e) Date: Jul. 9, 1996

[87] PCT Pub. No.: WO95/19350

PCT Pub. Date: Jul. 20, 1995

[30] Foreign Application Priority Data

Jan. 17, 1994 [DE] Germany ............................ 44 01 098

[51] Int. Cl.[7] ........................ A61K 31/42; C07D 263/10

[52] U.S. Cl. .......................... 514/374; 548/237; 548/238; 548/239

[58] Field of Search ............................ 514/374; 548/237, 548/239, 238

[56] References Cited

U.S. PATENT DOCUMENTS

| | | | |
|---|---|---|---|
| 3,901,906 | 8/1975 | Kozlik | 260/307 |
| 5,141,948 | 8/1992 | Miyamoto et al. | 514/374 |
| 5,478,855 | 12/1995 | Suzuki et al. | 514/374 |
| 5,578,625 | 11/1996 | Suzuki et al. | 514/374 |
| 5,631,014 | 5/1997 | Ishida et al. | 514/374 |
| 5,686,393 | 11/1997 | Lahm et al. | 548/239 |
| 5,807,877 | 9/1998 | Lantzsch et al. | 514/374 |

FOREIGN PATENT DOCUMENTS

WO96-22283 7/1996 WIPO .

OTHER PUBLICATIONS

Yamada et al. Chem Abstr. vol. 121, p. 1172 Entry 205334a, Oct. 1994.

Miyamoto et al. Chem Abstr. vol. 117 p. 745 Entry 131181n, 1992.

Lahm et al. Chem. Abstr. vol. 123, Entry 198780 Abstracting WO 95–04726, 1995.

Mencke et al Chem Abstr vol. 126 Entry 117963, 1996.

*Primary Examiner*—Richard L. Raymond
*Assistant Examiner*—Brenda Coleman
*Attorney, Agent, or Firm*—Norris McLaughlin & Marcus

[57] ABSTRACT

The invention relates to novel diphenyloxazoline derivatives of the formula (I)

(I)

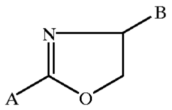

in which a) A represents tri- to pentasubstituted phenyl and B represents substituted phenyl or b) A represents mono- or disubstituted phenyl and B represents at least trisubstituted phenyl, but where at least one substituent is not fluorine, chlorine, bromine, $C_1$–$C_6$-alkyl or -alkoxy, to a number of processes for their preparation and to their use as pest control agents.

7 Claims, No Drawings

DIPHENYLOXAZOLINE DERIVATIVES

The invention relates to novel diphenyloxazoline derivatives, to a number of processes for their preparation and to their use for combating animal pests.

It is already known that certain oxazoline derivatives possess insecticidal and acaricidal properties (cf. e.g. EP-A 0 345 775 and EP-A 0 432 661). However, the activity of these previously known compounds does not give complete satisfaction in all areas of application, especially at low application rates and concentrations.

The novel diphenyloxazoline derivatives of the formula (I) have now been found (I)

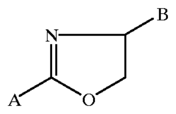

in which a) A represents tri- to pentasubstituted phenyl and
   B represents substituted phenyl or b) A represents mono- or disubstituted phenyl and
   B represents at least trisubstituted phenyl, but where at least one substituent is not fluorine, chlorine, bromine, $C_1$–$C_6$-alkyl or $C_1$–$C_6$-alkoxy.

It has also been found that diphenyloxazoline derivatives of the formula (I) are obtained by α) reacting amino alcohols of the formula (II)

(II)

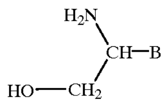

in which
B is as defined above
with a carboxylic acid of the formula (III)

A—COOH (III)

in which
A is as defined above,
with a dehydrating agent, optionally in the presence of a diluent; or β) reacting amido alcohols of the formula (IV)

(IV)

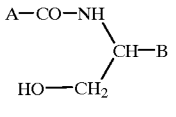

in which
A and B are as defined above
with a dehydrating agent, optionally in the presence of a diluent; or γ) reacting amide derivatives of the formula (V)

(V)

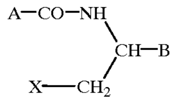

in which
A and B are as defined above; and
X represents a leaving group such as halogen, alkylsulfonyloxy or arylsulfonyloxy
with a base, optionally in the presence of a diluent.

It has also been found that diphenyloxazoline derivatives of the formula (I) are very highly suited to combating animal pests. They are distinguished in particular by high activity towards arthropods and nematodes.

Surprisingly, the diphenyloxazoline derivatives of the formula (I) according to the invention display a considerably improved activity towards animal pests than the previously known compounds which are closest in terms of constitution.

A general definition of the compounds according to the invention is given by the formula (I).

a) A preferably represents phenyl which is tri- to pentasubstituted by identical or different substituents consisting of halogen, $C_1$–$C_6$-alkyl, $C_1$–$C_6$-alkoxy, $C_1$–$C_6$-alkylthio, $C_1$–$C_6$-halogenoalkyl, $C_1$–$C_6$-halogenoalkoxy, $C_1$–$C_6$-halogenoalkylthio, nitro or cyano.

B preferably represents phenyl which is mono- to pentasubstituted by identical or different substituents consisting of
halogen,
$C_1$–$C_{18}$-alkyl,
$C_1$–$C_8$-alkoxy-$C_1$–$C_8$-alkyl,
$C_1$–$C_8$-halogenoalkoxy,
$C_1$–$C_4$-halogenoalkyl,
$C_1$–$C_{18}$-alkoxy which is optionally interrupted by 1–3 additional oxygen atoms,
$C_1$–$C_{18}$-alkylthio,
$C_1$–$C_8$-halogenoalkylthio, benzyliminooxymethyl which is optionally substituted by $C_1$–$C_4$-alkyl, or $C_3$–$C_6$-cycloalkyl and/or halogen,
cyclohexyl or cyclohexyloxy each of which are optionally substituted by $C_1$–$C_6$-alkyl, $C_1$–$C_6$-alkoxy, cyclohexyl or phenyl;
pyridyloxy which is optionally mono- or disubstituted by identical or different substituents consisting of halogen, $C_1$–$C_4$-alkyl or $C_1$–$C_4$-halogenoalkyl;
phenyl, benzyl, phenethyl, phenoxy, phenylthio, benzyloxy, phenethyloxy, benzylthio or styryl each of which is optionally mono- to trisubstituted by identical or different substituents consisting of $C_1$–$C_{12}$-alkyl, halogen, cyano, $C_1$–$C_4$-halogenoalkyl, $C_1$–$C_6$-alkoxy, $C_1$–$C_6$-halogenoalkoxy, $C_1$–$C_6$-alkoxy-$C_1$-$C_6$-alkyl, $C_1$–$C_6$-alkoxyethyleneoxy, $C_1$–$C_6$-alkylthio, $C_1$–$C_6$-halogenoalkylthio or trimethylsilyl.

b) A preferably represents phenyl which is mono- to disubstituted by identical or different substituents consisting of halogen, $C_1$–$C_6$-alkyl, $C_1$–$C_6$-alkoxy, $C_1$–$C_6$-alkylthio, $C_1$–$C_6$-halogenoalkyl, $C_1$–$C_6$-halogenoalkoxy, $C_1$–$C_6$-halogenoalkylthio, nitro or cyano.

B preferably represents phenyl which is tri- to pentasubstituted by identical or different substituents consisting of halogen, $C_1$–$C_{18}$-alkyl, $C_1$–$C_8$-alkoxy-$C_1$–$C_8$-alkyl, $C_1$–$C_8$-halogenoalkoxy, $C_1$–$C_4$-halogenoalkyl, $C_1$–$C_{18}$-alkoxy which is optionally interrupted by 1–3 additional oxygen atoms, $C_1$–$C_{18}$-alkylthio, $C_1$–$C_8$-halogenoalkylthio, benzyliminooxymethyl which is optionally substituted by $C_1$–$C_4$-alkyl, or $C_3$–$C_6$-cycloalkyl and/or halogen, cyclohexyl or cyclohexyloxy each of which are optionally substituted by $C_1$–$C_6$-alkyl, $C_1$–$C_6$-alkoxy, cyclohexyl or phenyl;

pyridyloxy which is optionally mono- or disubstituted by identical or different substituents consisting of halogen, $C_1$–$C_4$-alkyl or $C_1$–$C_4$-halogenoalkyl;

phenyl, benzyl, phenethyl, phenoxy, phenylthio, benzyloxy, phenethyloxy, benzylthio or styryl each of which is optionally mono- to trisubstituted by identical or different substituents consisting of $C_1$–$C_{12}$-alkyl, halogen, cyano, $C_1$–$C_4$-halogenoalkyl, $C_1$–$C_6$-alkoxy, $C_1$–$C_6$-halogenoalkoxy, $C_1$–$C_6$-alkoxy-$C_1$–$C_6$-alkyl, $C_1$–C6-alkoxyethyleneoxy, $C_1$–$C_6$-alkylthio, $C_1$–$C_6$-halogenoalkylthio or trimethylsilyl, but in which at least one substituent is not fluorine, chlorine, bromine, $C_1$–$C_6$-alkyl or $C_1$–$C_6$-alkoxy.

a) A particularly preferably represents phenyl which is tri- to pentasubstituted by identical or different substituents consisting of F, Cl, Br, $C_1$–$C_3$-alkyl, $C_1$–$C_3$-alkoxy, $C_1$–$C_3$-alkylthio, $C_1$–$C_2$-alkyl which is mono- to penta-substituted by identical or different substituents consisting of F and/or Cl, $C_1$–$C_4$-alkoxy which is mono- to pentasubstituted by identical or different substituents consisting of F and/or Cl, or $SCF_3$, $SCHF_2$, nitro or cyano.

B particularly preferably represents phenyl which is mono- to pentasubstituted by identical or different substituents consisting of F, Cl, Br, $C_1$–$C_{18}$-alkyl, $C_1$–$C_6$-alkoxy-$C_1$–$C_8$-alkyl, $C_1$–$C_8$-alkoxy which is mono- to hexasubstituted by identical or different substituents consisting of F and/or Cl, $C_1$–$C_2$-alkyl which is mono- to pentasubstituted by identical or different substituents consisting of F and/or Cl, $C_1$–$C_{18}$-alkoxy and —$(OC_2H_4)_{1\text{-}3}$—O-$C_1$–$C_6$-alkyl, $C_1$–$C_{12}$-alkylthio, $C_1$–$C_8$-alkylthio which is mono- to hexasubstituted by identical or different substituents consisting of F and/or Cl, the groups

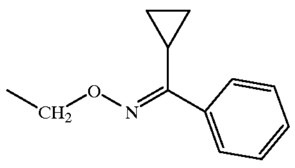

-continued

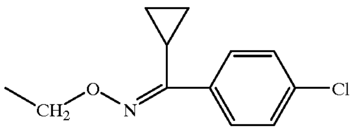

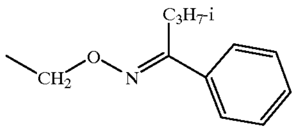

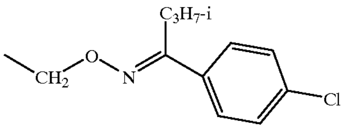
, cyclohexyl or cyclohexyloxy each of which is optionally substituted by $C_1$–$C_4$-alkyl, $C_1$–$C_4$-alkoxy, cyclohexyl or phenyl;

pyridyloxy which is optionally mono- or disubstituted by identical or different substituents consisting of F, Cl or $CF_3$;

phenyl, benzyl, phenethyl, phenoxy, phenylthio, phenethyloxy, benzyloxy, benzylthio or styryl each of which is optionally mono- to trisubstituted by identical or different substituents consisting of $C_1$–$C_{12}$-alkyl, F, Cl, Br, cyano, $CF_3$, $C_1$–$C_4$-alkoxy, $C_1$–$C_4$-alkoxy which is mono- to hexasubstituted by identical or different substituents consisting of F and/or Cl, or $C_1$–$C_4$-alkoxy-$C_1$–$C_4$-alkyl, $C_1$–$C_4$-alkoxyethyleneoxy, $C_1$–$C_4$-alkylthio, $C_1$–$C_4$-alkylthio which is mono- to hexasubstituted by identical or different substituents consisting of F and/or Cl, or trimethylsilyl.

b) A particularly preferably represents phenyl which is mono- to disubstituted by identical or different substituents consisting of F, Cl, Br, $C_1$–$C_3$-alkyl, $C_1$–$C_3$-alkoxy, $C_1$–$C_3$-alkylthio, $C_1$–$C_2$-alkyl which is mono- to penta-substituted by identical or different substituents consisting of F and/or Cl, $C_1$–$C_4$-alkoxy which is mono- to pentasubstituted by identical or different substituents consisting of F and/or Cl, or $SCF_3$, $SCHF_2$, nitro or cyano.

B particularly preferably represents phenyl which is tri- to pentasubstituted by identical or different substituents consisting of F, Cl, Br, $C_1$–$C_{18}$-alkyl, $C_1$–$C_6$-alkoxy-$C_1$–$C_8$-alkyl, $C_1$–$C_8$-alkoxy which is mono- to hexasubstituted by identical or different substituents consisting of F and/or Cl, $C_1$–$C_2$-alkyl which is mono- to pentasubstituted by identical or different substituents consisting of F and/or Cl, $C_1$–$C_{18}$-alkoxy and —$(OC_2H_4)_{1-3}$—O-$C_1$–$C_6$-alkyl, $C_1$–$C_{12}$-alkylthio, $C_1$–$C_8$-alkylthio which is mono- to hexasubstituted by identical or different substituents consisting of F and/or Cl, the groups

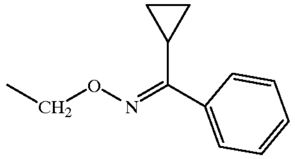

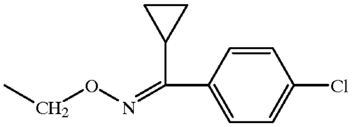

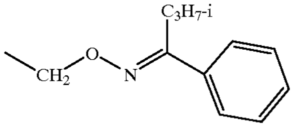

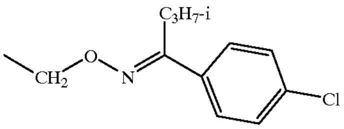
, cyclohexyl or cyclohexyloxy each of which is optionally substituted by $C_1$–$C_4$-alkyl, $C_1$–$C_4$-alkoxy, cyclohexyl or phenyl;

pyridyloxy which is optionally mono- or disubstituted by identical or different substituents consisting of F, Cl or $CF_3$;

phenyl, benzyl, phenethyl, phenoxy, phenylthio, phenethyloxy, benzyloxy, benzylthio or styryl each of which is optionally mono- to trisubstituted by identical or different substituents consisting of $C_1$–$C_{12}$-alkyl, F, Cl, Br, cyano, $CF_3$, $C_1$–$C_4$-alkoxy, $C_1$–$C_4$-alkoxy which is mono- to hexasubstituted by identical or different substituents consisting of F and/or Cl, or $C_1$–$C_4$-alkoxy-$C_1$–$C_4$-alkyl, $C_1$–$C_4$-alkoxyethyleneoxy, $C_1$–$C_4$-alkylthio, $C_1$–$C_4$-alkylthio which is mono- to hexasubstituted by identical or different substituents consisting of F and/or Cl, or trimethylsilyl;

in which at least one substituent is not fluorine, chlorine, bromine, $C_1$–$C_6$-alkyl or $C_1$–$C_6$-alkoxy.

The hydrocarbon radicals indicated above in the definition of the compound according to the invention, such as alkyl, are where possible—alone and in conjunction with heteroatoms, such as alkoxy—in each case straight-chain or branched.

TABLE 1a

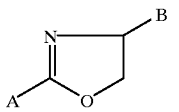
(I)

Compounds of Table 1a correspond to the formula (I) in which

A = 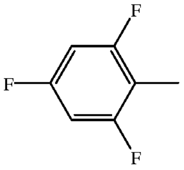 and B = as listed below:

| Compound No. | B |
|---|---|
| a1 | 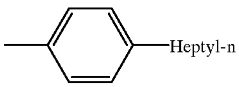 |
| a2 | 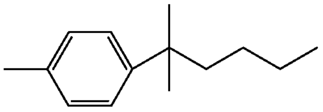 |
| a3 | 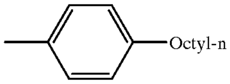 |
| a4 | 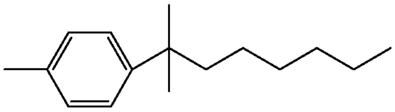 |
| a5 | 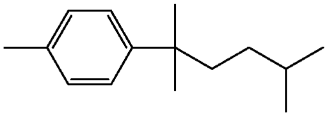 |
| a6 | 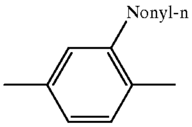 |
| a7 | 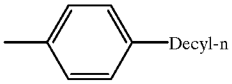 |
| a8 | 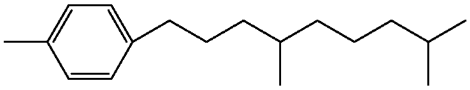 |

-continued
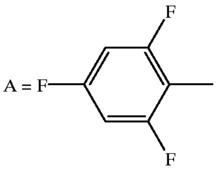 and B = as listed below:
| Compound No. | B |
| --- | --- |
| a9 | 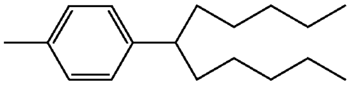 |
| a10 | 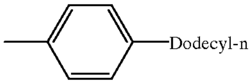 |
| a11 | 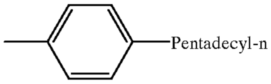 |
| a12 | 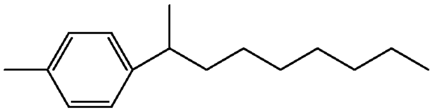 |
| a13 | 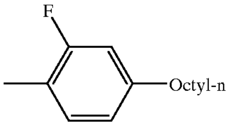 |
| a14 | 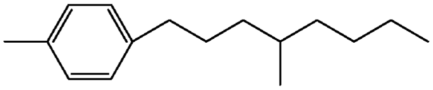 |
| a15 | 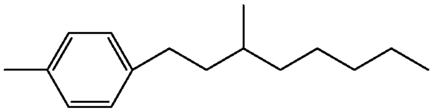 |
| a16 | 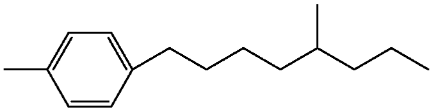 |
| a17 | 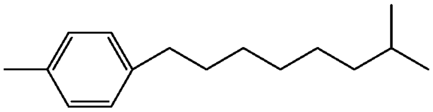 |
| a18 | 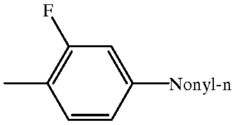 |
-continued
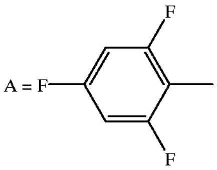 and B = as listed below:
| Compound No. | B |
| --- | --- |
| a19 | 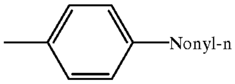 |
| a20 | 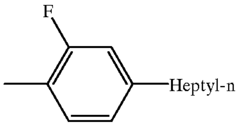 |
| a21 | 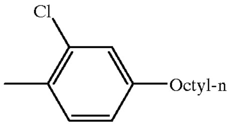 |
| a22 | 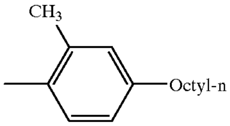 |
| a23 | 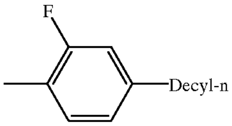 |
| a24 | 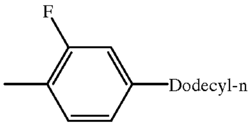 |
| a25 | 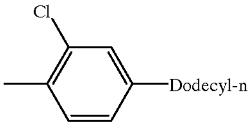 |
| a26 | 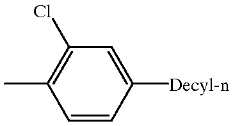 |
| a27 | 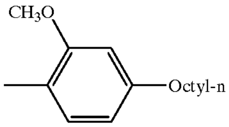 |

-continued
A = 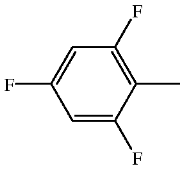 and B = as listed below:
| Compound No. | B |
| --- | --- |
| a28 | 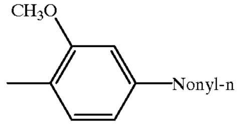 |
| a29 | 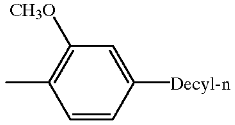 |
| a30 | 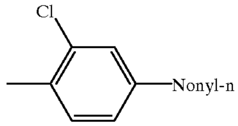 |
| a31 | 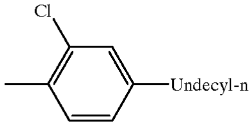 |
| a32 | 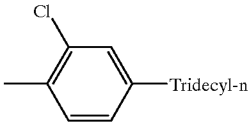 |
| a33 | 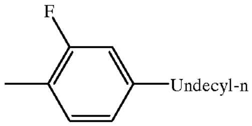 |
| a34 | 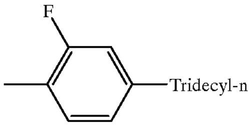 |
| a35 | 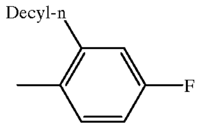 |
| a36 | 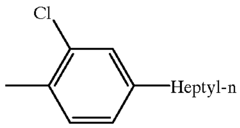 |
-continued
A = 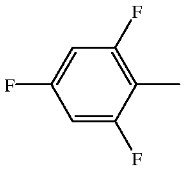 and B = as listed below:
| Compound No. | B |
| --- | --- |
| a37 | 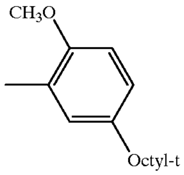 |
| a38 | 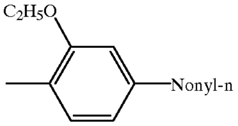 |
| a39 | 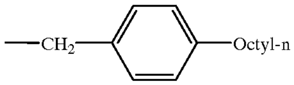 |
| a40 | 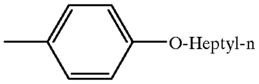 |
| a41 | 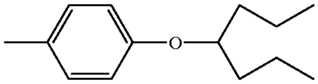 |
| a42 | 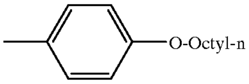 |
| a43 | 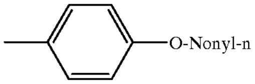 |
| a44 | 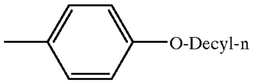 |
| a45 | 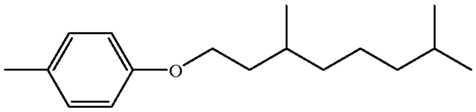 |
| a46 | 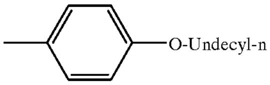 |

-continued
A = 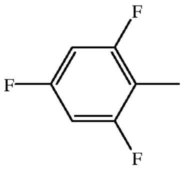 and B = as listed below:
| Compound No. | B |
|---|---|
| a47 | 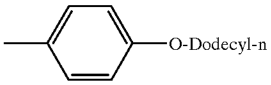 |
| a48 | 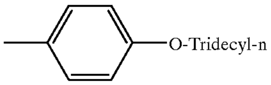 |
| a49 | 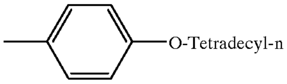 |
| a50 | 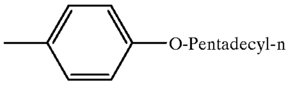 |
| a51 | 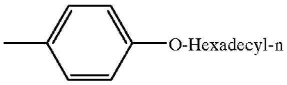 |
| a52 | 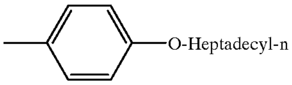 |
| a53 | 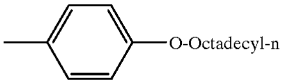 |
| a54 | 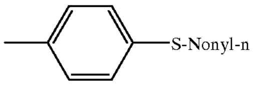 |
| a55 | 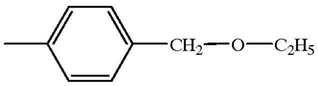 |
| a56 | 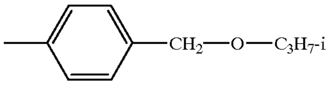 |
| a57 | 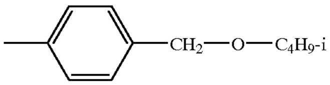 |
| a58 | 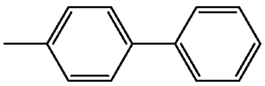 |
-continued
A = 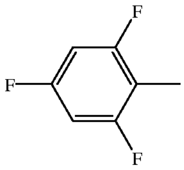 and B = as listed below:
| Compound No. | B |
|---|---|
| a59 | 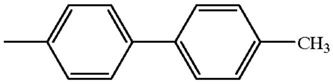 |
| a60 | 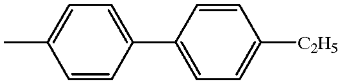 |
| a61 | 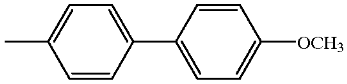 |
| a62 | 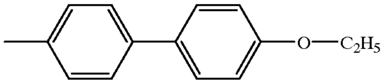 |
| a63 | 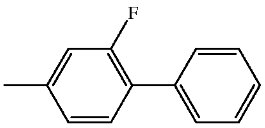 |
| a64 | 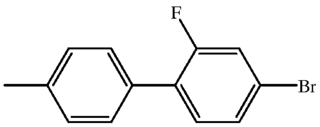 |
| a65 | 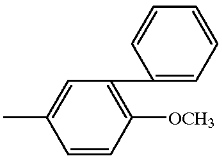 |
| a66 | 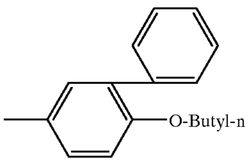 |
| a67 | 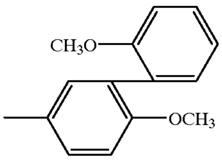 |

-continued
A = 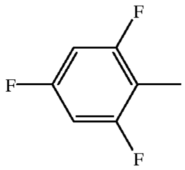 and B = as listed below:
| Compound No. | B |
| --- | --- |
| a68 | 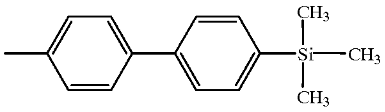 |
| a69 | 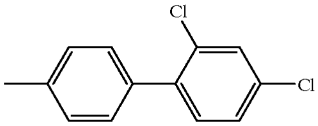 |
| a70 | 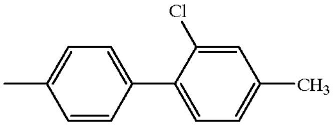 |
| a71 | 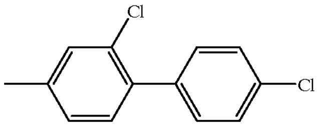 |
| a72 | 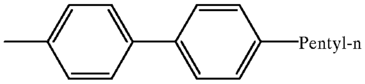 |
| a73 | 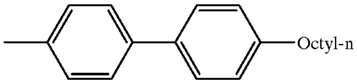 |
| a74 | 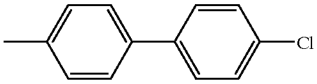 |
| a75 | 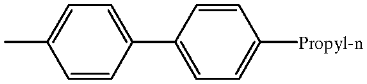 |
| a76 | 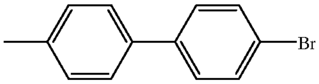 |
| a77 | 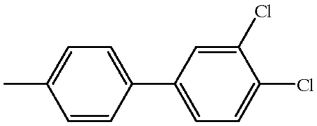 |
-continued
A = 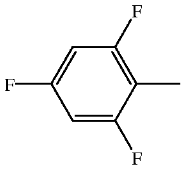 and B = as listed below:
| Compound No. | B |
| --- | --- |
| a78 | 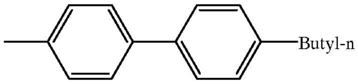 |
| a79 | 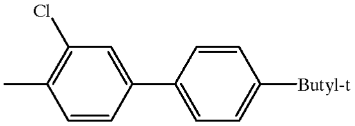 |
| a80 | 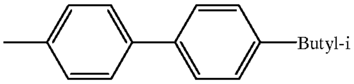 |
| a81 | 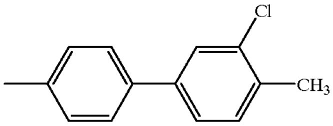 |
| a82 | 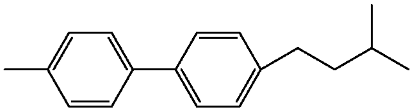 |
| a83 | 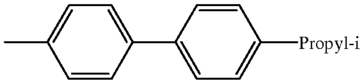 |
| a84 | 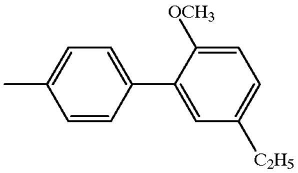 |
| a85 | 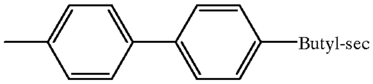 |
| a86 | 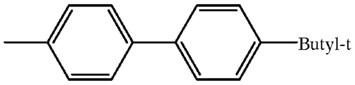 |
| a87 | 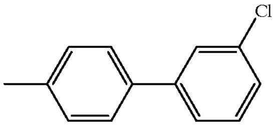 |

-continued
A = 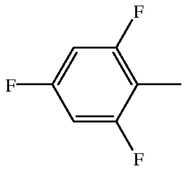 and B = as listed below:
| Compound No. | B |
|---|---|
| a88 | 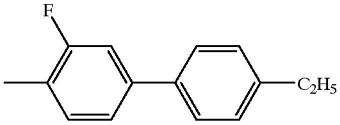 |
| a89 | 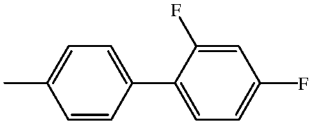 |
| a90 | 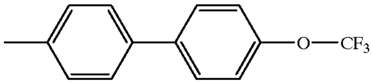 |
| a91 | 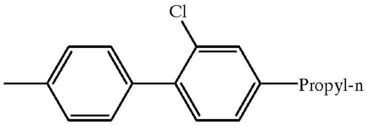 |
| a92 | 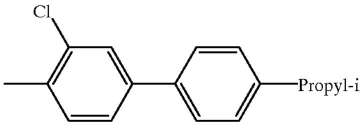 |
| a93 | 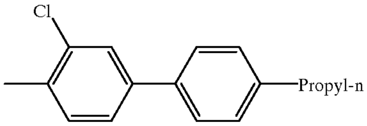 |
| a94 | 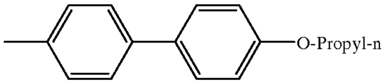 |
| a95 | 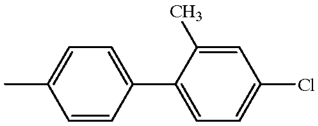 |
| a96 | 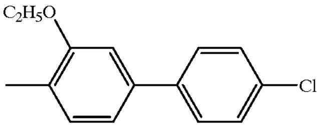 |
-continued
A = 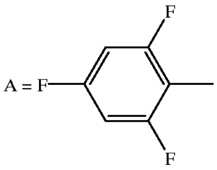 and B = as listed below:
| Compound No. | B |
|---|---|
| a97 | 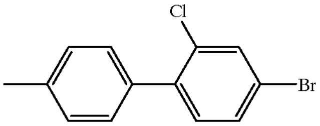 |
| a98 | 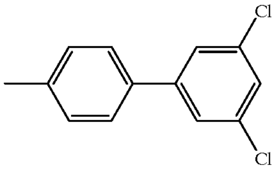 |
| a99 | 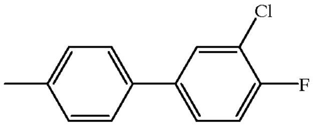 |
| a100 | 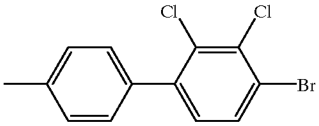 |
| a101 | 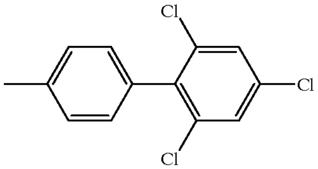 |
| a102 | 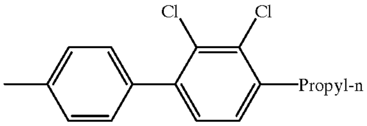 |
| a103 | 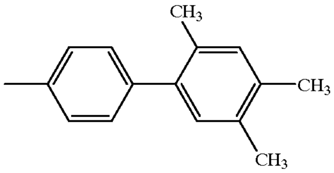 |
| a104 | 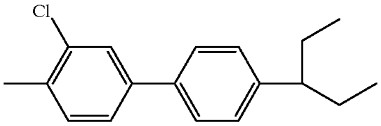 |

-continued
A = 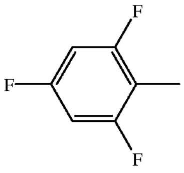 and B = as listed below:
| Compound No. | B |
|---|---|
| a105 | 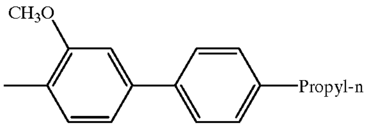 |
| a106 | 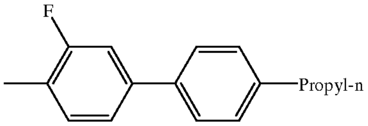 |
| a107 | 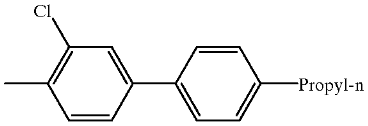 |
| a108 | 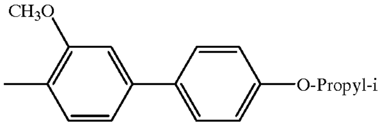 |
| a109 | 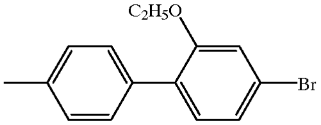 |
| a110 | 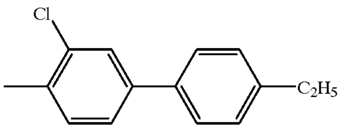 |
| a111 | 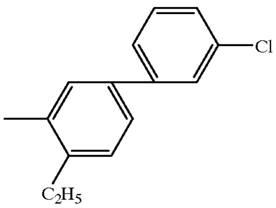 |
| a112 | 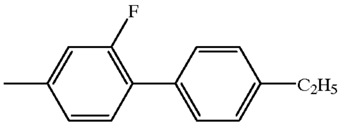 |
-continued
A = 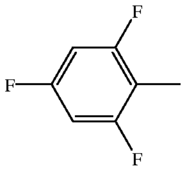 and B = as listed below:
| Compound No. | B |
|---|---|
| a113 | 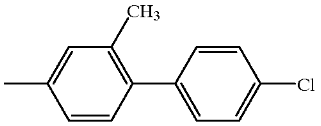 |
| a114 | 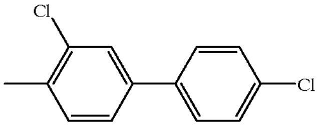 |
| a115 | 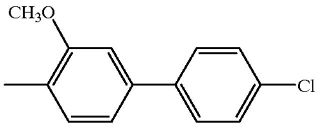 |
| a116 | 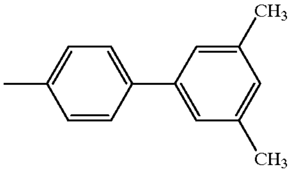 |
| a117 | 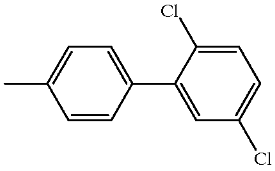 |
| a118 | 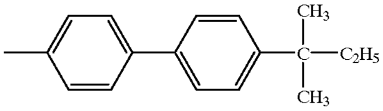 |
| a119 | 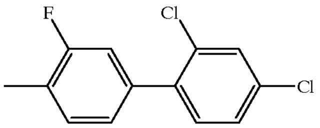 |
| a120 | 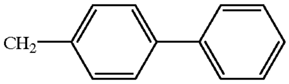 |
| a121 | 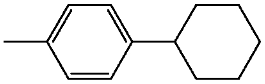 |

-continued
A = F 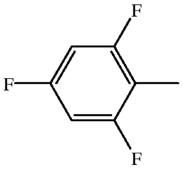 and B = as listed below:
| Compound No. | B |
|---|---|
| a122 | 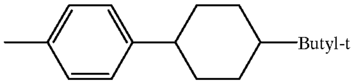 |
| a123 | 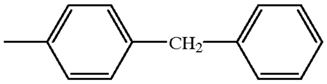 |
| a124 | 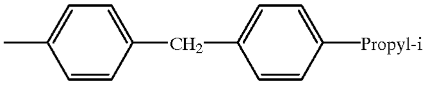 |
| a125 | 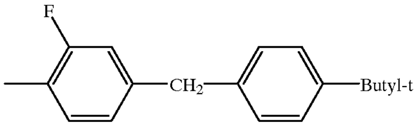 |
| a126 | 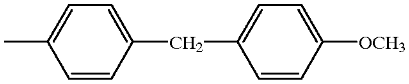 |
| a127 | 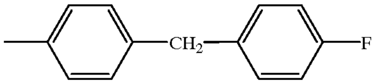 |
| a128 | 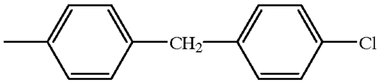 |
| a129 | 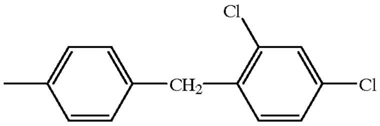 |
| a130 | 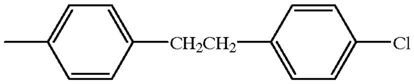 |
| a131 | 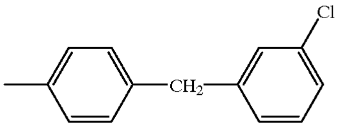 |
-continued
A = F 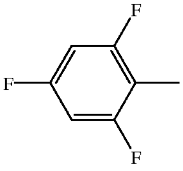 and B = as listed below:
| Compound No. | B |
|---|---|
| a132 | 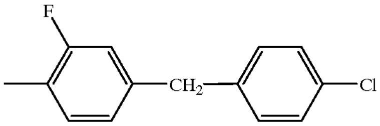 |
| a133 | 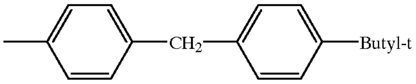 |
| a134 | 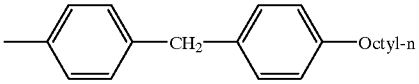 |
| a135 | 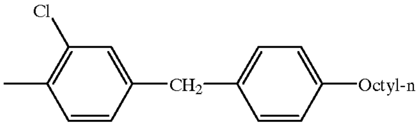 |
| a136 | 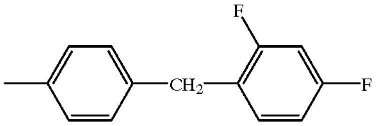 |
| a137 | 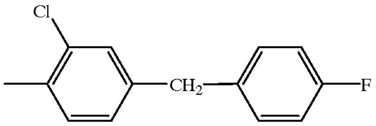 |
| a138 | 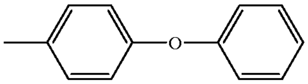 |
| a139 | 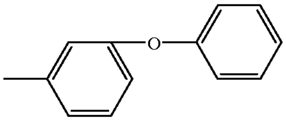 |
| a140 | 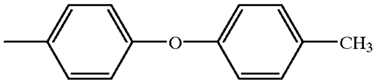 |
| a141 | 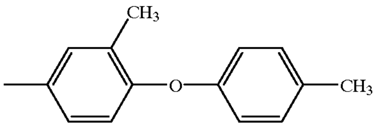 |

-continued
A = 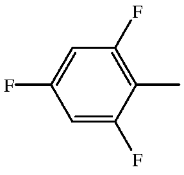 and B = as listed below:
| Compound No. | B |
|---|---|
| a142 | 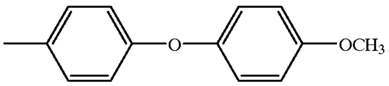 |
| a143 | 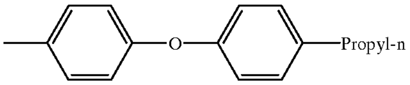 |
| a144 | 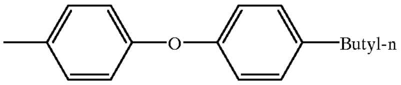 |
| a145 | 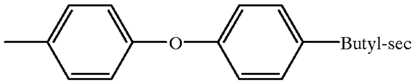 |
| a146 | 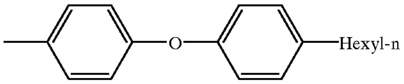 |
| a147 | 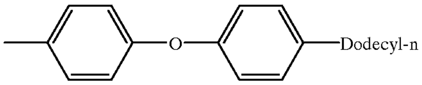 |
| a148 | 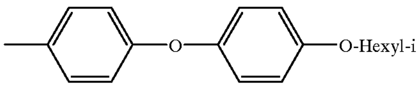 |
| a149 | 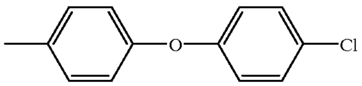 |
| a150 | 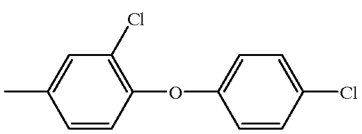 |
| a151 | 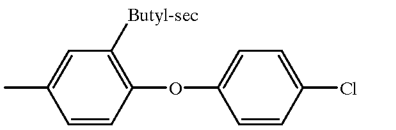 |
-continued
A = 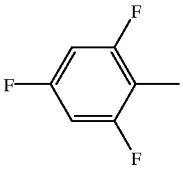 and B = as listed below:
| Compound No. | B |
|---|---|
| a152 | 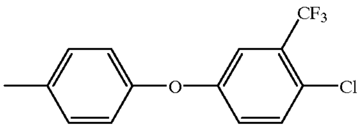 |
| a153 | 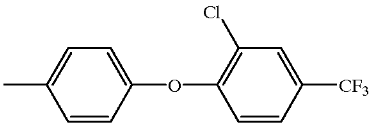 |
| a154 | 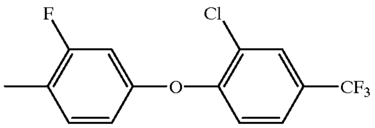 |
| a155 | 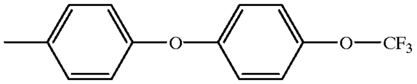 |
| a156 | 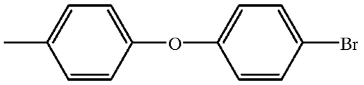 |
| a157 | 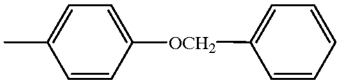 |
| a158 | 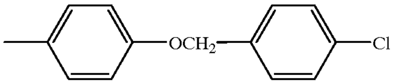 |
| a159 | 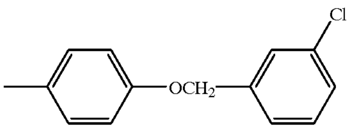 |
| a160 | 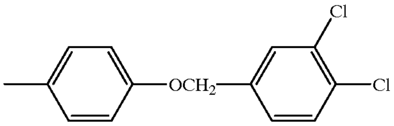 |
| a161 | 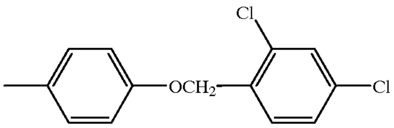 |

-continued
A = 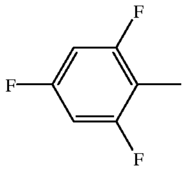 and B = as listed below:
| Compound No. | B |
|---|---|
| a162 | 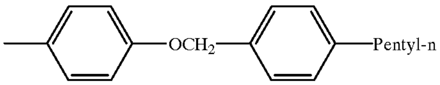 |
| a163 | 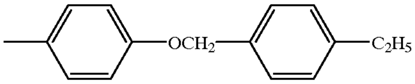 |
| a164 | 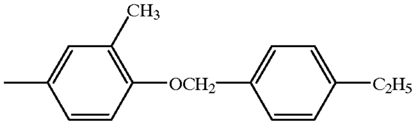 |
| a165 | 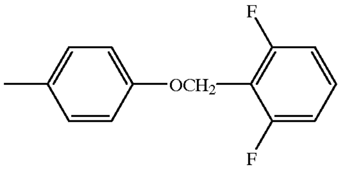 |
| a166 | 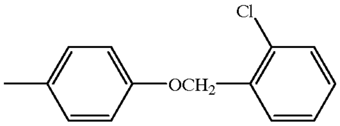 |
| a167 | 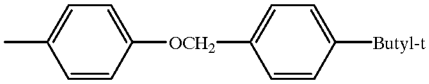 |
| a168 | 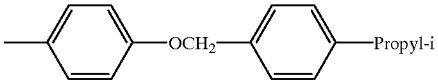 |
| a169 | 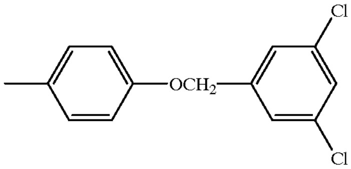 |
| a170 | 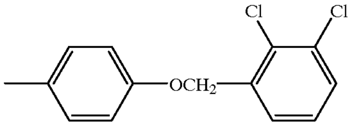 |
-continued
A = 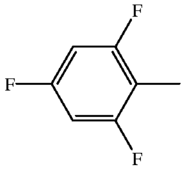 and B = as listed below:
| Compound No. | B |
|---|---|
| a171 | 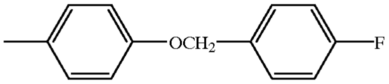 |
| a172 | 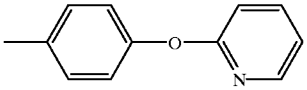 |
| a173 | 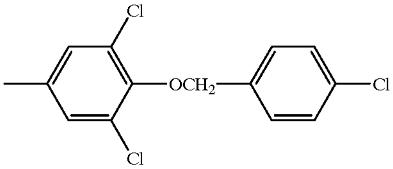 |
| a174 | 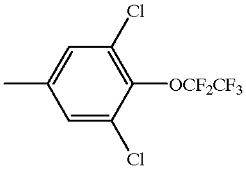 |
| a175 | 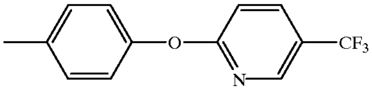 |
| a176 | 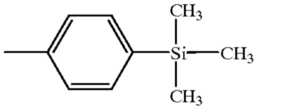 |
| a177 | 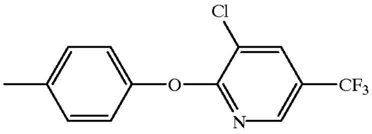 |
| a178 | 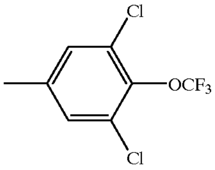 |

-continued
A = 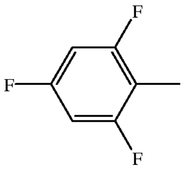 and B = as listed below:
| Compound No. | B |
|---|---|
| a179 | 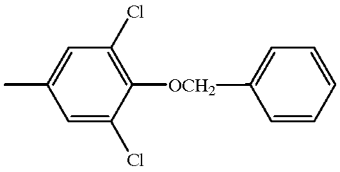 |
| a180 | 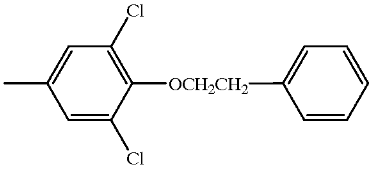 |
| a181 | 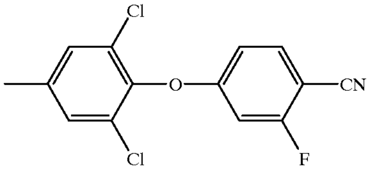 |
| a182 | 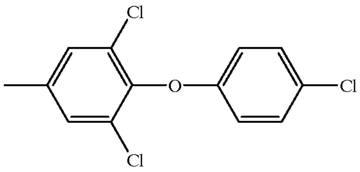 |
| a183 | 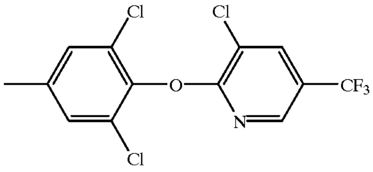 |
| a184 | 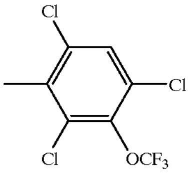 |
| a185 | 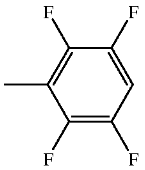 |
-continued
A = 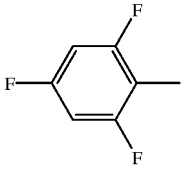 and B = as listed below:
| Compound No. | B |
|---|---|
| a186 | 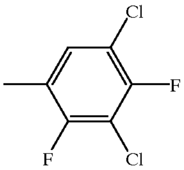 |
| a187 | 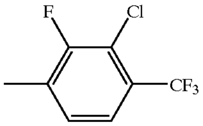 |
| a188 | 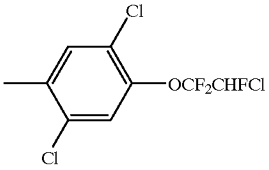 |
| a189 | 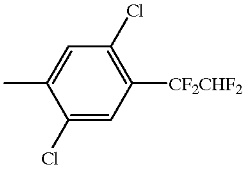 |
| a190 | 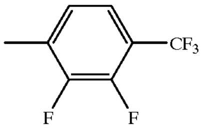 |
| a191 | 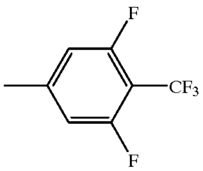 |
| a192 | 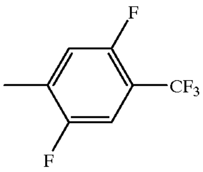 |

-continued

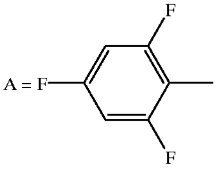

and B = as listed below:

| Compound No. | B |
|---|---|
| a193 | 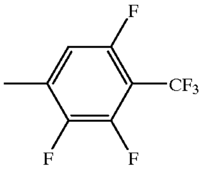 |
| a194 | 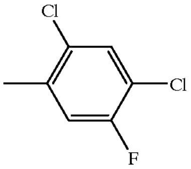 |
| a195 | 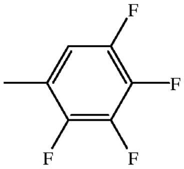 |
| a196 | 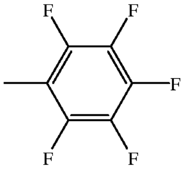 |
| a197 | 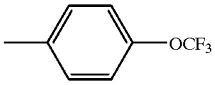 |
| a198 | 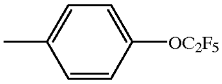 |

Table 2a

Table 2a contains the compounds of the general formula (I) in which

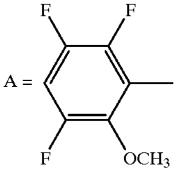

and B=as listed in Table 1a.

Table 3a

Table 3a contains the compounds of the general formula (I) in which

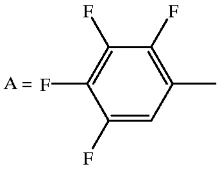

and B=as listed in Table 1a.

Table 4a

Table 4a contains the compounds of the general formula (I) in which

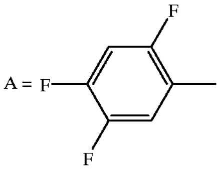

and B=as listed in Table 1a.

Table 5a

Table 5a contains the compounds of the general formula (I) in which

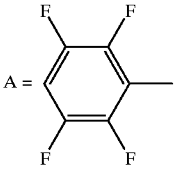

and B=as listed in Table 1a:

The examples of the compounds according to the invention of groups (b) are listed in Tables 1b–7b.

TABLE 1b

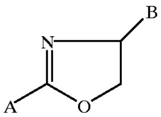

(I)

Table 1b contains the compounds of the general formula (I) in which

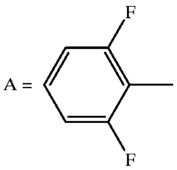

and B=as listed below:

| Compound No. | B |
|---|---|
| b1 | 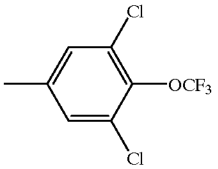 |
| b2 | 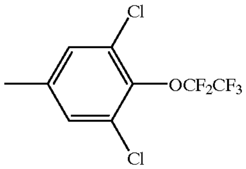 |
| b3 | 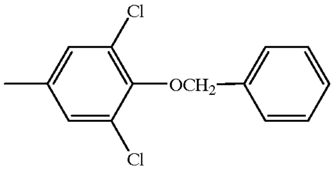 |
| b4 | 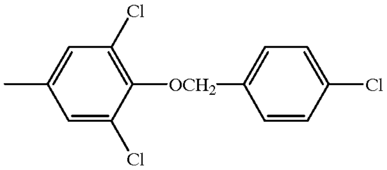 |
| b5 | 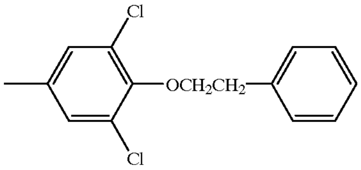 |
| b6 | 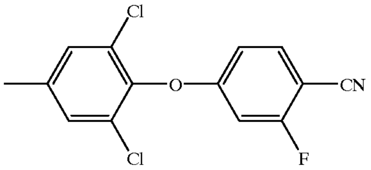 |
| b7 | 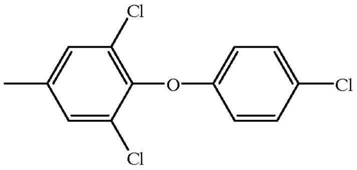 |
| b8 | 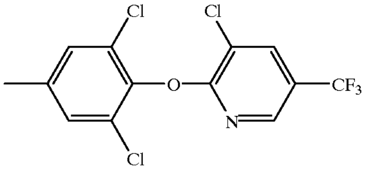 |

-continued
| Compound No. | B |
| --- | --- |
| b9 | 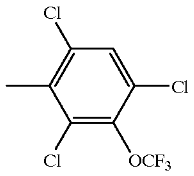 |
| b10 | 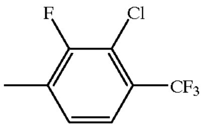 |
| b11 | 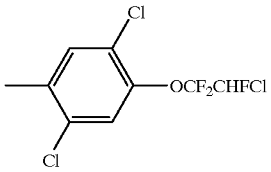 |
| b12 | 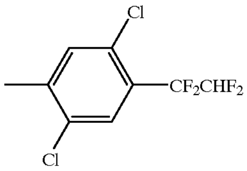 |
| b13 | 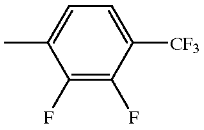 |
| b14 | 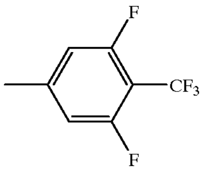 |
| b15 | 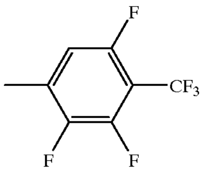 |
| b16 | 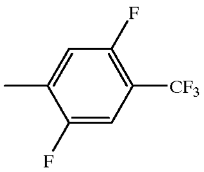 |

Table 2b

Table 2b contains the compounds of the general formula (I) in which

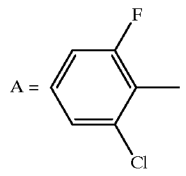

and B=as listed in Table 1b.

Table 3b

Table 3b contains the compounds of the general formula (I) in which

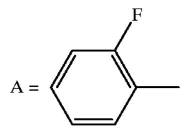

and B=as listed in Table 1b.

Table 4b

Table 4b contains the compounds of the general formula (I) in which

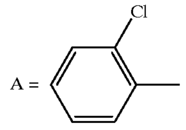

B=as listed in Table 1b.

Table 5b

Table 5b contains the compounds of the general formula (I) in which

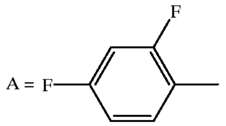

and B=as listed in Table 1b.

Table 6b

Table 6b contains the compounds of the general formula (I) in which

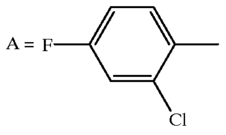

and B=as listed in Table 1b.

Table 7b

Table 7b contains the compounds of the general formula (I) in which

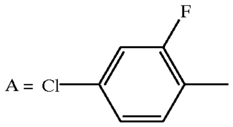

and B=as listed in Table 1b.

If for example, 2-amino-2-(4-t-butyl-phenyl)-1-ethanol and 2-methoxy-3,5,6-trifluoro-benzoic acid are used as starting materials for carrying out process (α) according to the invention, and polyphosphoric acid (PPA) is used as dehydrating agent, then the course of the reaction can be illustrated by the following equation:

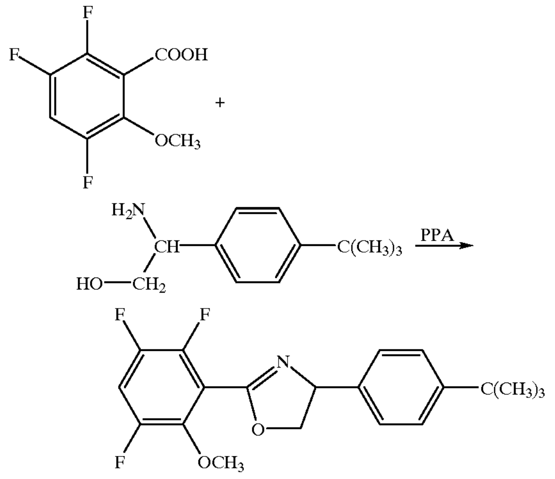

If, for example, N-[2-hydroxy-1-(4-t-butyl-phenyl)-ethyl]-2-methoxy-3,5,6-trifluorobenzamide is used as starting compound for carrying out process (β) according to the invention, and polyphosphoric acid (PPA) is used as dehydrating agent, then the course of the reaction can be illustrated by the following equation:

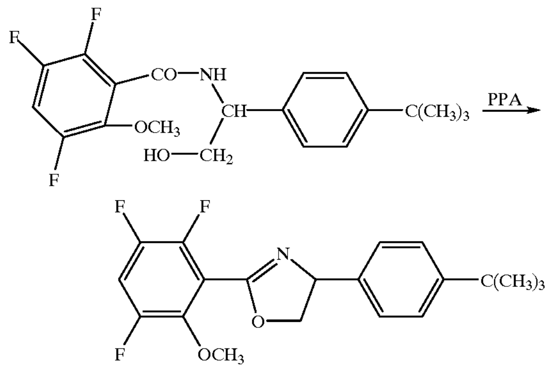

If, for example, N-[2-chloro-1-(4-t-butyl-phenyl)-ethyl]-2-methoxy-3,5,6-trifluoro-benzamide is used as starting compound and triethylamine is the base for carrying out the process (γ) according to the invention, then the course of the reaction can be illustrated by the following equation:

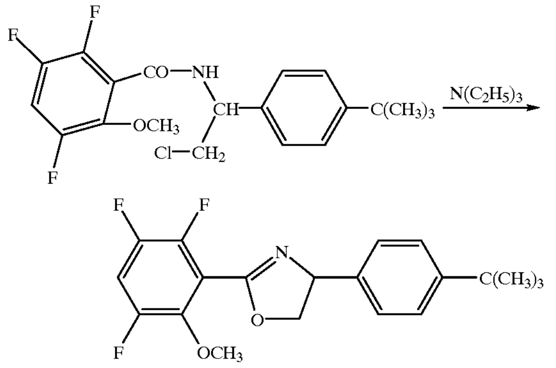

A general definition of the amino alcohols to be used as starting materials in process (α) according to the invention for the preparation of the compounds of the formula (I) is given by the formula (II). In the formula (II) B preferably or in particular has that meaning which has already been indicated above, in connection with the description of the compounds of the formula (I), as being preferred or particularly preferred for B.

The starting materials of the formula (II) are known and/or can be prepared by processes which are known per se, by reduction of the corresponding amino acids.

A general definition of the carboxylic acids also to be used as starting materials in process (α) according to the invention for the preparation of the compounds of the formula (I) is given by the formula (III). In the formula (III) A preferably or in particular has that meaning which has already been indicated above, in connection with the description of the compounds of the formula (I), as being preferred or particularly preferred for A.

The starting materials of the formula (III) are known chemicals of organic synthesis.

Processes (α) and (β) according to the invention are carried out using a dehydrating agent. The dehydrating agents which are customary in organic chemistry can be employed. Preferred possibilities for use are sulfuric acid, polyphosphoric acid (PPA), phosphorus(V) oxide, dicyclohexylcarbodiimide (DCC), phosphorus(V) sulfide and the system triphenylphosphine/triethylamine/tetrachloromethane.

Diluents which are suitable for carrying out processes (α) to (γ) according to the invention are the conventional organic solvents. Preferred possibilities for use are aliphatic, alicyclic or aromatic, optionally halogenated hydrocarbons, for example benzine, benzene, toluene, xylene, chlorobenzene, dichlorobenzene, petroleum ether, hexane, cyclohexane, dichloromethane, chloroform, tetrachloromethane; ethers such as diethyl ether, diisopropyl ether, dioxane, tetrahydrofuran or ethylene glycol dimethyl or diethyl ether; ketones such as acetone, butanone or methyl isobutyl ketone; nitriles such as acetonitrile, propionitrile, benzonitrile; amides such as N,N-dimethylformamide and N,N-dimethylacetamide, N-methyl-pyrrolidone or hexamethylphosphoric triamide; esters such as methyl acetate or ethyl acetate, and also sulfoxides such as dimethyl sulfoxide, and optionally alcohols such as methanol or ethanol.

When carrying out process (α) according to the invention the reaction temperatures can be varied over a relatively broad range. The process is in general carried out at temperatures of between 0° C. and 150° C., preferably at temperatures of between 10° C. and 100° C.

Process (α) according to the invention is generally carried out under atmospheric pressure. However, it is also possible to work under elevated or reduced pressure—generally at between 0.1 bar and 10 bar.

In order to carry out process (α) according to the invention, the particular starting materials required are generally employed in approximately equimolar quantities. However, it is also possible to use one of the two components employed in each case in a relatively large excess. The reactions are generally carried out in a suitable diluent in the presence of a dehydrating agent, and the reaction mixture is stirred for several hours at the particular temperature required. The mixture is worked up by conventional methods.

In a particular embodiment of process (α) according to the invention it is also possible to employ corresponding nitrites instead of the carboxylic acids of the formula (III), in which case a catalyst such as, for example, zinc(II) chloride is preferably used instead of dehydrating agent.

A general definition of the amido alcohols to be used as starting materials in process (β) according to the invention for the preparation of the compounds of the formula (I) is given by the formula (IV). In the formula (IV) A and B preferably or in particular have those meanings which have already been indicated above, in connection with the description of the compounds of the formula (I), as being preferred or particularly preferred for A and B.

The starting materials of the formula (IV) are known and/or can be prepared by processes which are known per se.

The amido alcohols of the formula (IV) are obtained, for example, by reacting acyl chlorides, derived from the carboxylic acids of the formula (III), with amino alcohols of the formula (II) in the presence of an acid-binding agent such as, for example, triethylamine, pyridine, potassium carbonate, sodium hydroxide or potassium t-butylate, and optionally in the presence of a diluent such as, for example, toluene, chlorobenzene, acetone or acetonitrile, at temperatures of between 0° C. and 100° C.

When carrying out process (β) according to the invention the reaction temperatures can be varied over a relatively broad range. The process is in general carried out at temperatures of between −20° C. and +150° C., preferably at temperatures between 0° C. and 100° C.

Process (β) according the invention is generally carried out under atmospheric pressure. However, it is also possible to work under elevated or reduced pressure—in general at between 0.1 bar and 10 bar.

To carry out process (β) according to the invention for the preparation of the compounds of the formula (I) requires the use, per mole of amido alcohol of the formula (IV), of in general from 1 to 20 mol, preferably from 1 to 5 mol, of dehydrating agent.

In a preferred embodiment of process (β) according to the invention the amido alcohol of the formula (IV) is placed in a diluent and the dehydrating agent is then metered in. The reaction mixture is stirred at the required temperature until the end of the reaction and is then worked up in a conventional manner.

A general definition of the amide derivatives to be used as starting materials in process (γ) according to the invention for the preparation of the compounds of the formula (I) is given by the formula (V). In the formula (V) A and B preferably or in particular have those meanings which have already been given, in connection with the description of the compounds of the formula (I), as being preferred or particularly preferred for A and B; X preferably represents fluorine, chlorine, bromine, iodine, $C_1$–$C_4$-alkyl-sulfonyloxy, phenylsulfonyloxy or tolylsulfonyloxy, especially chlorine, bromine, methylsulfonyloxy or tolylsulfonyloxy.

The starting materials of the formula (V) are known and/or can be prepared by processes which are known per se.

The amide derivatives of the formula (V) are obtained, for example, by reacting corresponding amido alcohols of the formula (IV) with halogenating agents such as, for example, thionyl chloride or phosphorus(V) chloride, or with sulfonylating agents such as, for example, methanesulfonyl chloride or p-toluenesulfonyl chloride, in a conventional manner.

Process (γ) according to the invention is carried out in the presence of a base. In this context all conventional inorganic or organic bases are suitable. Preferred possibilities for use are alkali metal or alkaline earth metal hydrides, hydroxides, amides, alcoholates, acetates, carbonates and hydrogen carbonates, for example sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, potassium hydrogen carbonate or ammonium carbonate, and also tertiary amines such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

When carrying out process (γ) according to the invention the reaction temperatures can be varied over a relatively broad range. The process is in general carried out at temperatures of between −20° C. and +150° C., preferably at temperatures between 0° C. and 100° C.

Process (γ) according to the invention is generally carried out under atmospheric pressure. However, it is also possible to work under elevated or reduced pressure—in general of between 0.1 bar and 10 bar.

To carry out process (γ) according to the invention for the preparation of the compounds of the formula (I) requires the use, per mole of amide derivative of the formula (V), of in general from 1 to 3 mol, preferably from 1.0 to 1.5 mol, of a base.

In a preferred embodiment of the process (γ) according to the invention the amide derivative of the formula (V) and a base are mixed in a suitable diluent; the mixture is stirred at the required temperature until the end of the reaction and is then worked up in a conventional manner.

The active compounds of the formula (I) are suitable for combating animal pests, preferably arthropods and nematodes, in particular insects and arachnida, which are encountered in agriculture, in forestry, in the protection of stored products and of materials, and in the hygiene field. They are active against normally sensitive and resistant species and against all or individual stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus*, Gryllotalpa spp., *Locusta migratoria migratorioides, Melanoplus differentialis* and *Schistocerca gregaria.*

From the order of the Dermaptera, for example, *Forficula auricularia.*

From the order of the Isoptera, for example, Reticulitermes spp.

From the order of the Anoplura, for example, *Phylloxera vastatrix*, Pemphigus spp., *Pediculus humanus corporis*, Haematopinus spp. and Linognathus spp.

From the order of the Mallophaga, for example, Trichodectes spp. and Damalinea spp.

From the order of the Thysanoptera, for example, *Hercinothrips femoralis* and *Thrips tabaci.*

From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae*, Myzus spp., *Phorodon humuli, Rhopalosiphum padi*, Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae*, Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea*, Lymantria spp. *Bucculatrix thurberiella, Phyllocnistis citrella*, Agrotis spp., Euxoa spp., Feltia spp., *Earias insulana*, Heliothis spp., *Spodoptera exigua, Mamestra brassicae, Panolis flammea, Prodenia litura*, Spodoptera spp., Trichoplusiani, *Carpocapsa pomonella*, Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.* From the order of the Coleoptera, for example, *Anobium punctatum, Rhizopertha dominica, Acanthoscelides obtectus, Bruchidius obtectus, Hylotrupes bajulus, Agelastica alni, Leptinotarsa decemlineata, Phaedon cochleariae*, Diabrotica spp., *Psylliodes chrysocephala, Epilachna varivestis*, Atomaria spp., *Oryzaephilus surinamensis*, Anthonomus spp., Sitophilus spp., *Otiorrhynchus sulcatus, Cosmopolites sordidus, Ceuthorrhynchus assimilis, Hypera postica*, Dermestes spp., Trogoderma spp., Anthrenus spp., Attagenus spp., Lyctus spp., *Meligethes aeneus*, Ptinus spp., *Niptus hololeucus, Gibbium psylloides*, Tribolium spp., *Tenebrio molitor*, Agriotes spp., Conoderus spp., *Melolontha melolontha, Amphimallon solstitialis* and *Costelytra zealandica.*

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster*, Musca spp., Fannia spp., *Calliphora erythrocephala*, Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit*, Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp.

From the order of the Arachnida, for example, *Scorpio maurus* and *Latrodectus mactans.*

From the order of the Acarina, for example, *Acarus siro*, Argas spp., Ornithodoros spp., *Dermanyssus gallinae, Eriophyes ribis, Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp. and Tetranychus spp.

The phytoparasitic nematodes include Pratylenchus spp., *Radopholus similis, Ditylenchus dipsaci, Tylenchulus semipenetrans*, Heterodera spp., Meloidogyne spp., Aphelenchoides spp., Longidorus spp., Xiphinema spp. and Trichodorus spp.

At appropriate application rates the compounds according to the invention also display a fungicidal activity.

The active compounds can be converted to the customary formulations, such as solutions, emulsions, wettable powders, suspensions, powders, dusts, pastes, soluble powders, granules, suspension/emulsion concentrates, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is, liquid solvents, and/or solid carriers, optionally with the use of surface-active agents, that is emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulphonates as well as albumen hydrolysis products; as dispersing agents there are suitable: for example lignin-sulfite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, attractants, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The following compounds may be mentioned:

acrinathrin, alphamethrin, betacyfluthrin, bifenthrin, brofenprox, cis-resmethrin, clocythrin, cycloprothrin, cyfluthrin, cyhalothrin, cypermethrin, deltamethrin, esfenvalerate, etofenprox, fenpropathrin, fenvalerate, flucythrinate, fluvalinate, lambda-cyhalothrin, permethrin, pyresmethrin, pyrethrum, silafluofen, tralomethrin, zetamethrin, alanycarb, bendiocarb, benfuracarb, bufencarb, butocarboxim, carbaryl, cartap, ethiofencarb, fenobucarb, fenoxycarb, isoprocarb, methiocarb, methomyl, metolcarb, oxamyl, pirimicarb, promecarb, propoxur, terbam, thiodicarb, thiofanox, trimethacarb, XMC, xylylcarb, acephate, azinphos A, azinphos M, bromophos A, cadusafos, carbophenothion, chlorfenvinphos, chlormephos, chlorpyrifos, chlorpyrifos M, cyanophos, demeton M, demeton-S-methyl, demeton S, diazinon, dichlorvos, dicliphos, dichlorfenthion, dicrotophos, dimethoate, dimethylvinphos, dioxathion, disulfoton, edifenphos, ethion, etrimphos, fenitrothion, fenthion, fonophos, formothion, heptenophos, iprobenfos, isazophos, isoxathion, phorate, malathion, mecarbam, mervinphos, mesulfenphos, methacrifos, methamidophos, naled, omethoate, oxydemeton M, oxydeprofos, parathion A, parathion M, phenthoate, phorate, phosalone, phosmet, phosphamdon, phoxim, pirimiphos A, pirimiphos M, propaphos, prothiophos, prothoate, pyraclophos, pyridaphenthion, quinalphos, salithion, sebufos, sulfotep, sulprofos, tetrachlorvinphos, temephos, thiomethon, thionazin, trichlorfon, triazophos, vamidothion, buprofezin, chlorfluazuron, diflubenzuron, flucycloxuron, flufenoxuron, hexaflumuron, pyriproxifen, tebufenozide, teflubenzuron, triflumuron, imidacloprid, nitenpyram, N-[(6-chloro-3-pyridyl)methyl]-N'-cyano-N-methyl-ethaneimideamide (NI-25), abamectin, amitrazin, avermectin, azadirachtin, bensultap, Bacillus thuringiensis, cyromazine, diafenthiuron, emamectin, ethofenprox, fenpyrad, fipronil, flufenprox, lufenuron, metaldehyd, milbemectin, pymetrozine, tebufenpyrad, triazuron, aldicarb, bendiocarb, benfuracarb, carbofuran, carbosulfan, chlorethoxyfos, cloethocarb, disulfoton, ethophrophos, etrimphos, fenamiphos, fipronil, fonofos, fosthiazate, furathiocarb, HCH, isazophos, isofenphos, methiocarb, monocrotophos, nitenpyram, oxamyl, phorate, phoxim, prothiofos, pyrachlofos, sebufos, silafluofen, tebupirimphos, tefluthrin, terbufos, thiodicarb, thiafenox, azocyclotin, butylpyridaben, clofentezine, cyhexatin, diafenthiuron, diethion, emamectin, fenazaquin, fenbutatin oxide, fenothiocarb, fenpropathrin, fenpyrad, fenpyroximate, fluazinam, fluazuron, flucycloxuron, flufenoxuron, fluvalinate, fubfenprox, hexythiazox, ivemectin, methidathion, monocrotophos, moxidectin, naled, phosalone, profenofos, pyraclofos, pyridaben, pyrimidifen, tebufenpyrad, thuringiensin, triarathene and 4-bromo-2-(4-chlorophenyl)-1-(ethoxymethyl)-5-(trifluoromethyl)-1H-pyrrole-3-carbonitrile (AC 303630).

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

The active compounds according to the invention are not only active against plant, hygiene and stored product pests, but also, in the veterinary medicine sector, against animal parasites (ectoparasites and endoparasites), such as scaly ticks, argasidae, scab mites, trombidae, flies (stinging and sucking), parasitic fly larvae, lice, hair lice, bird lice, fleas and worms which live as endoparasites. For example, they have an outstanding activity against ticks such as, for example, *Boophilus microplus*.

The active compounds of the formula (I) according to the invention are also suitable for the combating of arthropods which infest useful animals in agriculture such as, for example, cattle, sheep, goats, horses, pigs, donkeys, camels, buffalo, rabbits, hens, turkeys, ducks, geese, bees, other domestic animals such as, for example, dogs, cats, cage birds, aquarium fish and so-called experimental animals such as, for example, hamsters, guinea pigs, rats and mice. The aim of combating these arthropods is to reduce fatalities and reductions in yield (in meat, milk, wool, skins, eggs, honey, etc.) so that the use of the active compound according to the invention renders the keeping of animals more economic and more simple.

In the veterinary sector the active compounds according to the invention are employed in a known manner by enteral administration in the form of, for example, tablets, capsules, potions, drenches, granules, pastes, boli, by the feed-through method, suppositories, by parenteral administration, for example by injection (intramuscular, subcutaneous, intravenous, intraperitoneal etc.), by implants, by nasal administration, by dermal application in the form, for example, of dipping or bathing, spraying, pouring on and spotting on, washing, dusting and with the aid of shaped articles which contain active compound, such as neck bands, ear tags, tail tags, limb bands, halters, marking devices and the like.

The preparation and the use of the substances according to the invention is illustrated by the following examples:

PREPARATION EXAMPLES

Example 1

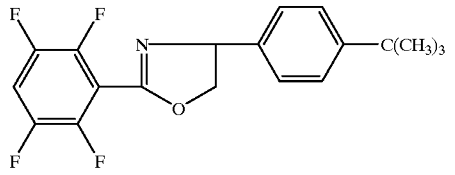

(Process γ)

0.75 g (6.7 mmol) of potassium tert-butylate is added to a solution of 2.0 g (5.2 mmol) of N-[1-(4-tert-butylphenyl)-2-chloroethyl]-2,3,5,6-tetrafluorobenzamide in 30 ml of tetrahydrofuran, and the mixture is stirred at 50° C. After 3 hours the reaction mixture is poured into water and extracted with methylene chloride. The organic extracts are washed with water, dried over magnesium sulfate and subsequently concentrated in vacuo. The residue is purified by column chromatography (eluent: chloroform).

0.8 g (44.7% of theory) of 4-(4-tert-butylphenyl)-2-(2,3,5,6-tetrafluorophenyl)-1,3-oxazoline is obtained with a partition coefficient log p (octanol/water) of 4.70 (pH: 7.4).

PREPARATION OF THE STARTING PRODUCT

Example (V-1)

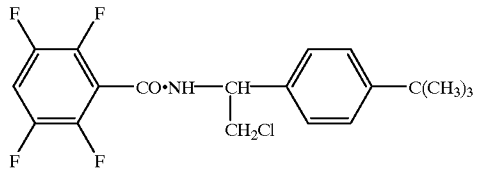

2.1 g (5.7 mmol) of N-[1-(4-tert-butylphenyl)-2-hydroxyethyl)-2,3,5,6-tetrafluorobenzamide in 50 ml of toluene are heated under reflux with 5 ml of thionyl chloride for 18 hours. Subsequently excess thionyl chloride and the solvent are removed in vacuo.

2.2 g (100% of theory) of N-[1-(4-tert-butylphenyl)-2-chloroethyl]-2,3,5,6-tetrafluorobenzamide are obtained, which is reacted further directly.

Example (IV-1)

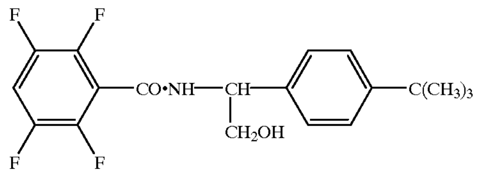

1.6 g (7.5 mmol) of 2,3,5,6-tetrafluorobenzoyl chloride dissolved in 10 ml of methylene chloride is added dropwise with stirring at 20° C. to a solution of 1.45 g (7.5 mmol) of 2-amino-2-(4-tert-butylphenyl)-ethanol and 0.75 g (7.5 mmol) of triethylamine in 20 ml of methylene chloride. The mixture is boiled overnight and then diluted with methylene chloride and washed with water, and the organic phase is concentrated in vacuo. The residue is stirred with a little n-pentane and filtered off with suction.

2.3 g (83.1% of theory) of N-[1-(4-tert-butylphenyl)-2-hydroxyethyl]-2,3,5,6-tetrafluorobenzamide are obtained of melting point 158–160° C.
In a corresponding way and in accordance with the general instructions for preparation, the following diphenyloxazoline derivatives of the formula (I) are obtained:
(I)
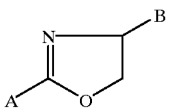
| Ex.-No. | A | B | Physical Constants |
|---|---|---|---|
| 2 | 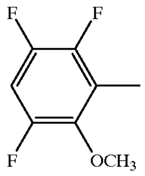 | 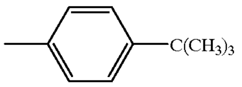 | log p(pH 7,5) = 4.59 |
| 3 | 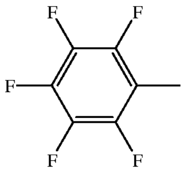 | 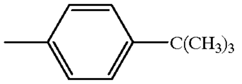 | log p (pH 7,5) = 5.12 |
| 4 | 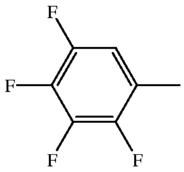 | 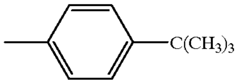 | log p (pH 7,5) = 4.78 |
| 5 | 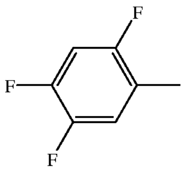 | 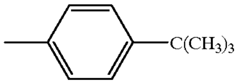 | log p (pH 7,5) = 4.78 |
| 6 | 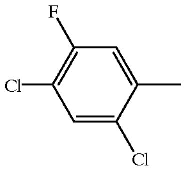 | 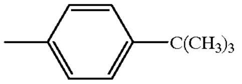 | log p (pH 7,5) = 5.65 |
| 7 | 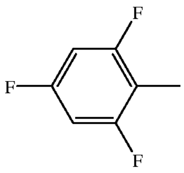 | 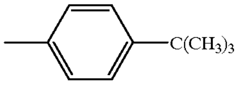 | log p (pH 7,5) = 4.43 |
| 8 | 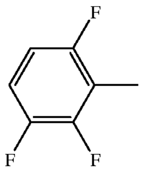 | 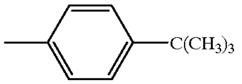 | log p (pH 7,5) = 4.45 |

-continued

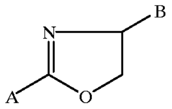

(I)

| Ex.-No. | A | B | Physical Constants |
|---|---|---|---|
| 9 | 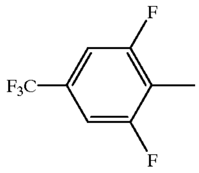 | 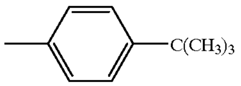 | log p (pH 7,5) = 5.13<br>m.p. = 120–122° C. |
| 10 | 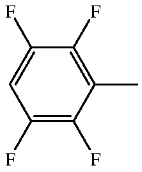 | 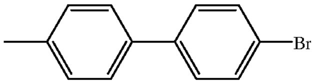 | m.p. 118–120° C. |
| 11 | 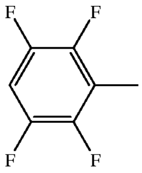 | 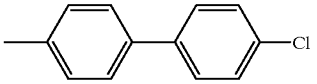 | m.p. 120–122° C. |
| 12 | 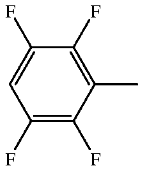 | 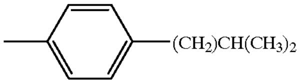 | log p (pH 7.5) = 5.35 |
| 13 | 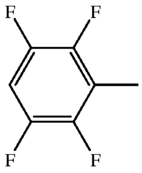 | 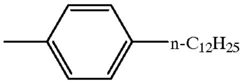 | m.p. 44° C. |
| 14 | 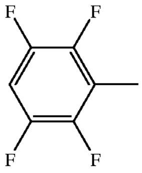 | 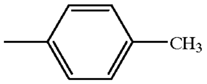 | log p (pH 7.5) = 3.69 |

Example A

Tetranychus Test (OP resistant/dipping treatment)
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with emulsifier-containing water to the desired concentrations.

Bean plants (*Phaseolus vulgaris*) which are heavily infested with all developmental stages of the red spider mite *Tetranychus urticae* are dipped in a preparation of the active compound of the desired concentration.

After the desired time, the action in percent is determined. 100% means that all the spider mites have been killed, 0% means that none of the spider mites have been killed.

In this test, for example the compounds from Preparation Examples 1, 2 and 5 exhibit a degree of mortality of 98% after 7 days, at an exemplary concentration of active compound of 0.01%.

Example B

Phaedon Larvae Test

Solvent: 3 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*), as long as the leaves are still moist.

After the desired time, the destruction in % is determined. 100% means that all the beetle larvae have been killed; 0% means that none of the beetle larvae have been killed.

In this test the compounds from Preparation Examples 1 and 2 exhibit a degree of mortality of 65% at a concentration of active compound of 0.1%.

We claim:

1. A diphenyloxazoline compound of the formula (I)

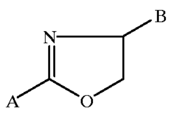

in which

A represents phenyl substituted 3 to 5 times by identical or different substituents selected from the group consisting of F, Cl, Br, $C_1$–$C_3$-alkoxy, $C_1$–$C_2$-alkyl which is substituted 1 to 5 times by identical or different substituents selected from the group consisting of F or Cl, and B represents phenyl substituted 1 to 5 times which is substituted by identical or different substituents selected from the group consisting of F, Cl, Br, $C_1$–$C_{18}$-alkyl, $C_1$–$C_6$-alkoxy-$C_1$–$C_8$-alkyl, $C_1$–$C_8$-alkoxy substituted 1 to 6 times by identical or different substituents selected from the group consisting of F or Cl, $C_1$–$C_2$-alkyl substituted 1 to 5 times by identical or different substituents selected from the group consisting of F or Cl, $C_1$–$C_{18}$-alkoxy and —$(OC_2H_4)_{1\text{-}3}$—O-$C_1$–$C_6$-alkyl, $C_1$–$C_8$-alkylthio substituted 1 to 6 times by identical or different substituents selected from the group consisting of F or Cl, the groups

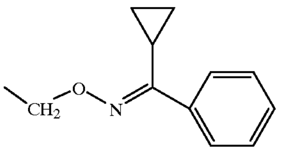

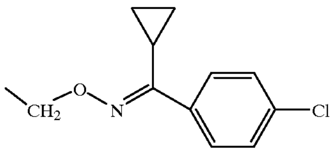

-continued

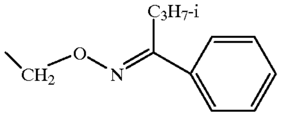

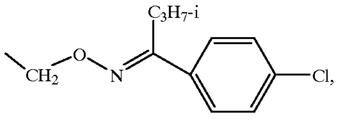

, cyclohexyl or cyclohexyloxy each of which is optionally substituted by $C_1$–$C_4$-alkyl, $C_1$–$C_4$-alkoxy, cyclohexyl or phenyl; phenyl, benzyl, phenethyl, phenoxy, phenylthio, phenethyloxy, benzyloxy, benzylthio or styryl each of which is optionally substituted 1 to 3 times by identical or different substituents selected from the group consisting of $C_1$–$C_{12}$-alkyl, F, Cl, Br, cyano, $CF_3$, $C_1$–$C_4$-alkoxy, $C_1$–$C_4$-alkoxy substituted 1 to 6 times by identical or different substituents selected from the group consisting of F, Cl, $C_1$–$C_4$-alkoxy-$C_1$–$C_4$-alkyl, $C_1$–$C_4$-alkoxyethyleneoxy, $C_1$–$C_4$-alkylthio, $C_1$–$C_4$-alkylthio substituted 1 to 6 times by identical or different substituents selected from the group consisting of F and Cl.

2. A composition for killing insects, arachnids and nematodes comprising an arthropodically and nematodically effective amount of at least one compound of the formula (I) as claimed in claim 1 and a diluent.

3. A method of killing insects, arachnids and nematodes, which comprises applying an arthropodically and nematodically effective amount of a compound of the formula (I) as claimed in claim 1 to arthropods and nematodes or to a habitat thereof.

4. A diphenyloxazoline compound of the formula (I) as claimed in claim 1, in which A represents phenyl substituted 3 to 5 times by identical or different substituents selected from the group consisting of F, Cl, Br, $C_1$–$C_3$-alkoxy, $C_1$–$C_2$-alkyl which is substituted 1 to 5 times by identical or different substituents selected from the group consisting of F or Cl, and B represents phenyl substituted 1 to 5 times which is substituted by identical or different substituents selected from the group consisting of F, Cl, Br, $C_1$–$C_{18}$-alkyl, $C_1$–$C_6$-alkoxy-$C_1$–$C_8$-alkyl, $C_1$–$C_8$-alkoxy substituted 1 to 6 times by identical or different substituents selected from the group consisting of F or Cl, $C_1$–$C_2$-alkyl substituted 1 to 5 times by identical or different substituents selected from the group consisting of F or Cl, $C_1$–$C_{18}$-alkoxy, cyclohexyl which is optionally substituted by $C_1$–$C_4$-alkyl; phenyl, benzyl, phenethyl, phenoxy, phenethyloxy or benzyloxy, each of which is optionally substituted 1 to 3 times by identical or different substituents selected from the group consisting of $C_1$–$C_{12}$-alkyl, F, Cl, Br, cyano, $CF_3$, $C_1$–$C_4$-alkoxy, $C_1$–$C_4$-alkoxy substituted 1 to 6 times by identical or different substituents selected from the group consisting of F or Cl.

5. A diphenyloxazoline compound of the formula (I) as claimed in claim 1, in which A represents phenyl substituted 3 to 5 times by identical or different substituents selected from the group consisting of F, Cl, Br, $C_1$–$C_3$-alkoxy, $C_1$–$C_2$-alkyl which is substituted 1 to 5 times by identical or different substituents selected from the group consisting of F or Cl, and B represents phenyl substituted 1 to 5 times which is substituted by identical or different substituents selected from the group consisting of $C_1$–$C_{12}$-alkyl or phenyl, which is optionally substituted 1 to 3 times by identical or different substituents selected from the group consisting of $C_1$–$C_{12}$-alkyl, F, Cl or Br.

6. A diphenyloxazoline compound of the formula (I) as claimed in claim 1, in which A represents phenyl substituted 3 to 5 times by identical or different substituents selected from the group consisting of F, Cl, Br, $C_1$–$C_3$-alkoxy, $C_1$–$C_2$-alkyl which is substituted 1 to 5 times by identical or different substituents selected from the group consisting of F or Cl, and B represents phenyl substituted 1 time by phenyl which is optionally substituted 1 to 3 times by identical or different substituents selected from the group consisting of $C_1$–$C_{12}$-alkyl, F, Cl or Br.

7. A diphenyloxazoline compound of the formula

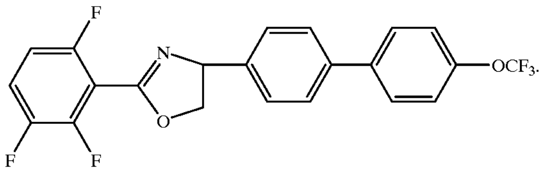

* * * * *